United States Patent [19]
Luber et al.

[11] Patent Number: 5,795,294
[45] Date of Patent: Aug. 18, 1998

[54] PROCEDURE FOR THE CORRELATION OF DIFFERENT COORDINATE SYSTEMS IN COMPUTER-SUPPORTED, STEREOTACTIC SURGERY

[75] Inventors: Joachim Luber, Essingen; Arvids Mackevics, Aalen, both of Germany

[73] Assignee: Carl-Zeiss-Stiftung, Heidenheim, Germany

[21] Appl. No.: 452,752

[22] Filed: May 30, 1995

[30] Foreign Application Priority Data

May 21, 1994 [DE] Germany ............ 44 17 944.8

[51] Int. Cl.⁶ .................. A61B 5/05; A61B 19/00
[52] U.S. Cl. .............. 600/407; 600/429; 606/130; 128/898
[58] Field of Search .............. 364/413.01, 413.13, 364/415; 356/375; 128/898, 653.1; 606/130; 600/425, 429, 407

[56] References Cited

U.S. PATENT DOCUMENTS

| | | |
|---|---|---|
| 4,481,616 | 11/1984 | Matey .................. 369/58 |
| 4,722,056 | 1/1988 | Roberts et al. ........... 364/413 |
| 4,991,579 | 2/1991 | Allen .................. 128/653.1 |
| 5,099,846 | 3/1992 | Hardy . |
| 5,332,181 | 7/1994 | Schweizer et al. ........ 248/123.1 |
| 5,345,087 | 9/1994 | Luber et al. ............ 250/561 |
| 5,359,417 | 10/1994 | Muller et al. ........... 356/375 |
| 5,491,510 | 2/1996 | Gove .................. 348/77 |
| 5,513,005 | 4/1996 | Muller et al. ........... 356/375 |

FOREIGN PATENT DOCUMENTS 4134481  4/1993  Germany .

*Primary Examiner*—Mickey Yu
*Assistant Examiner*—Kelly O'Hara

[57] ABSTRACT

In a procedure for correlating different coordinate systems in computer-supported, stereotactic surgery, without the use of additional referencing markers, partial topographical information is collected by means of a surgical microscope mounted on a carrier system, and this partial topographical information is spatially correlated with the diagnostic data generated prior to surgery using a suitable correlation algorithm.

6 Claims, 4 Drawing Sheets

5,795,294

PROCEDURE FOR THE CORRELATION OF DIFFERENT COORDINATE SYSTEMS IN COMPUTER-SUPPORTED, STEREOTACTIC SURGERY

BACKGROUND OF THE INVENTION

1. Field of the Invention

The present invention relates to a procedure for the correlation of different coordinate systems in computer-supported, stereotactic surgery without the use of additional so-called referencing markers.

In computer-supported, stereotactic surgery it is necessary to correlate different coordinate systems with each other when diagnostic data generated prior to surgery by means of an NMR tomograph, for example, is to be used for optimizing orientation during surgery. This is necessary, for example, if such pictorial information must be superposed on a image obtained of the surgical field. The current image of the surgical field may consist of the field of view seen in a surgical microscope, or of a monitor image generated with a video camera.

2. Discussion of Prior Art

Normally, the necessary correlation is performed by adopting a referencing procedure in which so-called referencing markers are measured on a patient, with the coordinate positions of these markers relative to the patient's coordinate system and relative to the diagnostic data coordinate system being known. Such marker measurement can be performed, for example, using a surgical microscope such as the one disclosed in German patent application 41 34 481 of the applicants' assignee, corresponding to U.S. Pat. No. 5,359,417.

As an alternative, the markers can also be measured by means of so-called laser pointers which are placed on the surgical microscope. The U.S. Pat. No. 5,279,309 discloses that such markers can be implemented in the form of miniature transmitters placed on the patient and located via appropriate detectors.

A disadvantage of all known procedures based on referencing using markers, however, is that these procedures are relatively time-consuming and must be repeated if the patient's position may have changed.

Also, it is always necessary to perform the imaging diagnostic procedures with these markers. This puts the patient under stress if the markers must be implanted as described, for example, in U.S. Pat. No. 5,178,164.

OBJECT OF THE INVENTION

It is therefore the objective of the present invention to provide a procedure which makes it possible to correlate the diagnostic data generated prior to surgery with the current topographical data of the patient by using a surgical microscope, without the need for measuring the coordinates or locating separate referencing markers. In particular, it is intended to improve the stereotactic application possibilities of a surgical microscope.

This problem is solved by a procedure for correlation of different coordinate systems in computer-supported stereotactic surgery without use of additional referencing markers that includes: using a surgical microscope mounted on a carrier system to obtain partial topographical information and spatially correlating the partial topographical information with diagnostic data generated prior to surgery via a correlation algorithm.

In accordance with the invention, no separate markers are now used to perform the correlation of different coordinate systems in a time-consuming referencing procedure. Instead, the surgical microscope mounted on a suitable carrier system is used directly for the acquisition of at least partial topographical information of the patient. The partial topographical information obtained with the surgical microscope is subsequently digitized and correlated with the diagnostic data records generated prior to surgery via known algorithms.

Totally different imaging procedures can be used in combination with the procedure according to the invention to obtain the diagnostic data records generated prior to surgery. As examples, the neutron magnetic resonance tomography (NMR), the positron emission tomography (PET), the magnet enzephalography (MEG) and the single photon emission computer tomography (SPECT) are specified here as modern diagnostic procedures, which can all be used on their own or in any combination.

Partial topographical information using the surgical microscope can be obtained in different ways. A suitable embodiment of the procedure according to the invention can be selected as a function of the desired outlay and the specific requirements.

The surgical microscope must be configurated in accordance with the procedure in question.

The time-consuming referencing procedures using separate referencing markers and the resulting complex operational procedures including the related patient stress involved if such markers need to be implanted, are no longer required.

Furthermore, the virtually automated acquisition of partial topographical information using the surgical microscope permits fast re-correlation of the different coordinate systems if the patient's current position or the position of parts of the patient's body has changed.

DESCRIPTION OF THE DRAWINGS

Further advantages and details of the procedure according to the invention and different embodiments thereof can be taken from the following description of examples based on the annexed figures in which.

DETAILED DESCRIPTION OF PREFERRED EMBODIMENTS

The acquisition of at least partial topographical information according to the invention using a surgical microscope mounted on a motorized carrier system can be performed in different ways. Different embodiments of the procedure according to the invention are described in the following on the basis of FIGS. 2–4.

Figure 1:
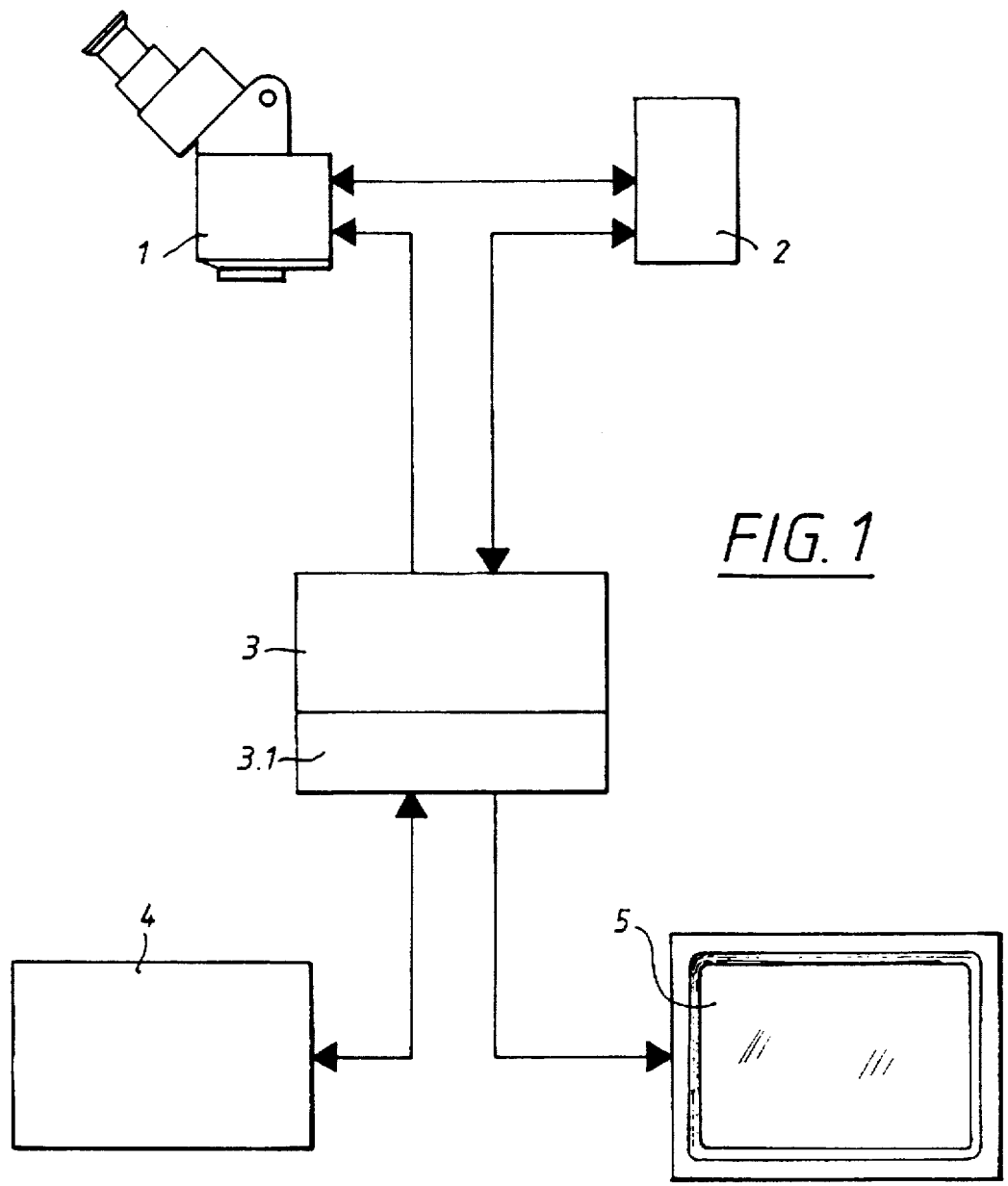
FIG. 1 shows a block diagram with the most important components required for performing the procedure according to the invention.

All described embodiments of the procedure according to the invention have in common the fundamental system configuration with the necessary basic components of a fixture suitable for this purpose. The most important required components are schematically shown in the block diagram of FIG. 1.

For performing the procedure according to the invention, a surgical microscope (1) is envisaged, this being mounted on a suitable carrier system (2)—shown only schematically—which in the illustrated example is motor-operated.

With the help of the carrier system (2), defined positioning in a known coordinate system of the surgical microscope (1) is possible in up to six spatial degrees of freedom. The standard degrees of freedom for the spatial positioning of the surgical microscope are three degrees of freedom in rotation and three in translation.

A suitable, multi-joint carrier system (2) which is motorized is disclosed in the German patent application 42 02 922 of the applicants' assignee, corresponding to U.S. Pat. No. 5,332,181. This comprises amongst others drives and encoder assigned to the respective joints, so that a central control unit (3) of the overall system can continuously determine the coordinate-related positions of the surgical microscope (1) together with the known geometry data of the carrier system (2) and the surgical microscope (1).

As an alternative to the known carrier system disclosed in German patent application 42 02 922, more simply configurated carrier systems can be used provided they permit defined spatial positioning of the surgical microscope on them and the acquisition of the respective coordinate position. It would be feasible, for example, to configurate certain embodiments of the procedure according to the invention without the drives in the individual joints and to position the carrier system manually or to provide an alternative position-reading system.

The surgical microscope (1) used features a generally known optical design and can also include a superimposing device via which images generated elsewhere or graphical illustrations can be superimposed on at least one of the stereoscopic observation beam paths via known beam splitting devices.

In addition, the surgical microscope (1) includes a position identification system based on an optical system, which permits active, high-precision measurement of the field of view plane under observation. For this purpose it is possible, for example, to integrate a laser triangulation measuring system in the surgical microscope optics, this measuring system permitting the precise determination of the coordinates of a point in the field of view plane.

As regards a preferred, suitable surgical microscope, reference is made expressly to the surgical microscope disclosed in German patent application 41 34 481 of the applicant.

As an alternative to a position detection system based on an optical system, other, preferably also non-tactic position detection systems may possibly be used according to the invention. The use of 3D ultrasonic sound digitizers would, for example, be possible.

In addition, a (previously mentioned) central control unit (3) in the form of a control computer is envisaged. The control unit (3) performs the entire control work and position detection of the carrier system and also processes the image information of the diagnostic data records generated prior to surgery which were digitized and filed in an appropriate image data base (4).

The central control unit (3) further comprises in input interface (3.1), e.g. in the form of a keyboard, by means of which the operator can perform the surgical planning, for example.

Figure 2:
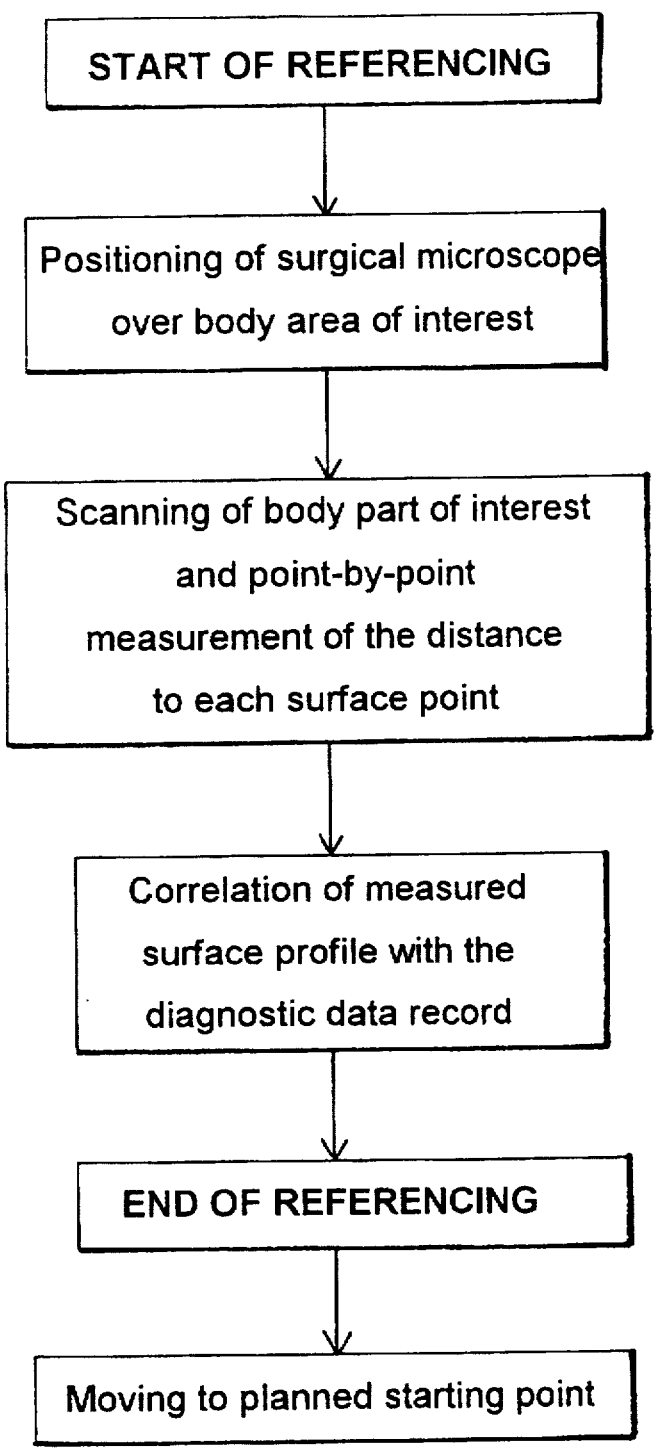
FIG. 2 shows a flow diagram of a first embodiment of the procedure according to the invention.

An initial example of the procedure according to the invention is now explained using the flow diagram in FIG. 2, in which the major procedural steps are listed. The surgical microscope mounted on the motorized carrier system in an initial embodiment of the procedure according to the invention is first moved in a defined way over the part of the patient's body which is of interest and to be subjected to correlation. For this, the body area in question is first selected and the surgical microscope is positioned over this area by means of the motorized carrier system.

The field of view plane of the surgical microscope is then moved in a scanning motion over the body area of interest. The scanning motion can be achieved by the operator manually controlling the maneuvering of the surgical microscope mounted on the motorized carrier system. As an alternative, defined positioning over the area in question can be obtained by the central control unit with specific, preselected positioning parameters. Such positioning parameters include, for example, preselection of the defined scanning range and the scanning speed, etc. During the scanning motion over the body area of interest, which is to be spatially correlated with the diagnostic data record generated prior to surgery, the position detection system of the surgical microscope continually defines point-by-point that distance between the object surface and the surgical microscope whose spatial coordinates are known to the central control unit as a result of the encoder information of the carrier system. In this way it is possible to record partial topographical information on body areas of the patient and to file this data in a digitized form. The topographical information obtained in this way thus consists in the present example in a three-dimensional surface profile, such as was generated from the different distances between the object surface and the surgical microscope over a certain surface area. The partial topographical information of the object area under observation or of interest thus obtained with the surgical microscope is subsequently correlated with the topographical information of the diagnostic data record generated prior to surgery, which also provides three-dimensional object information. For the correlation between the measured 3D profile and the diagnostic data record generated prior to surgery, known correlation algorithms, like the ones known in photogrammetry are used.

This embodiment of the procedure according to the invention requires neither separate marker on the patient, nor additional devices on the surgical microscope, if the previously mentioned surgical microscope of German patent application 41 34 481 is used, for example. The only demand on the surgical microscope used is that it must be able to measure the distance measurement of a point in the field of view and to transfer the signal to the central control unit.

The use of alternative surgical microscopes is another possibility in this embodiment of the procedure according to the invention. These surgical microscopes may, for example, be equipped with an active autofocus system which permits them to perform the required point-to-point distance measurement.

When the correlation of the patient's topography with the diagnostic data generated prior to surgery has been performed, the referencing procedure is completed and the surgical microscope is moved to the planned starting point for subsequent surgery.

Figure 3B:
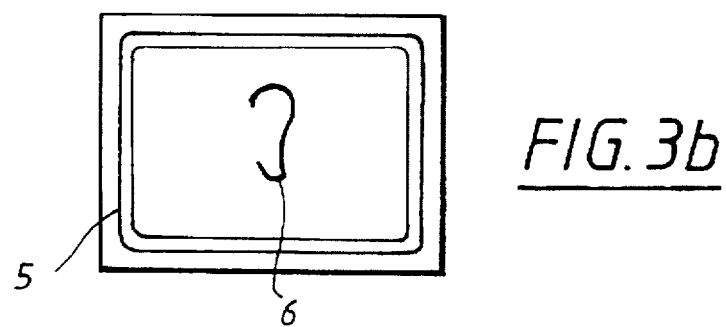
FIG. 3b shows the contours visible in the field of view of the surgical microscope which can be used for referencing in a second embodiment of the procedure according to the invention.
Figure 3A:
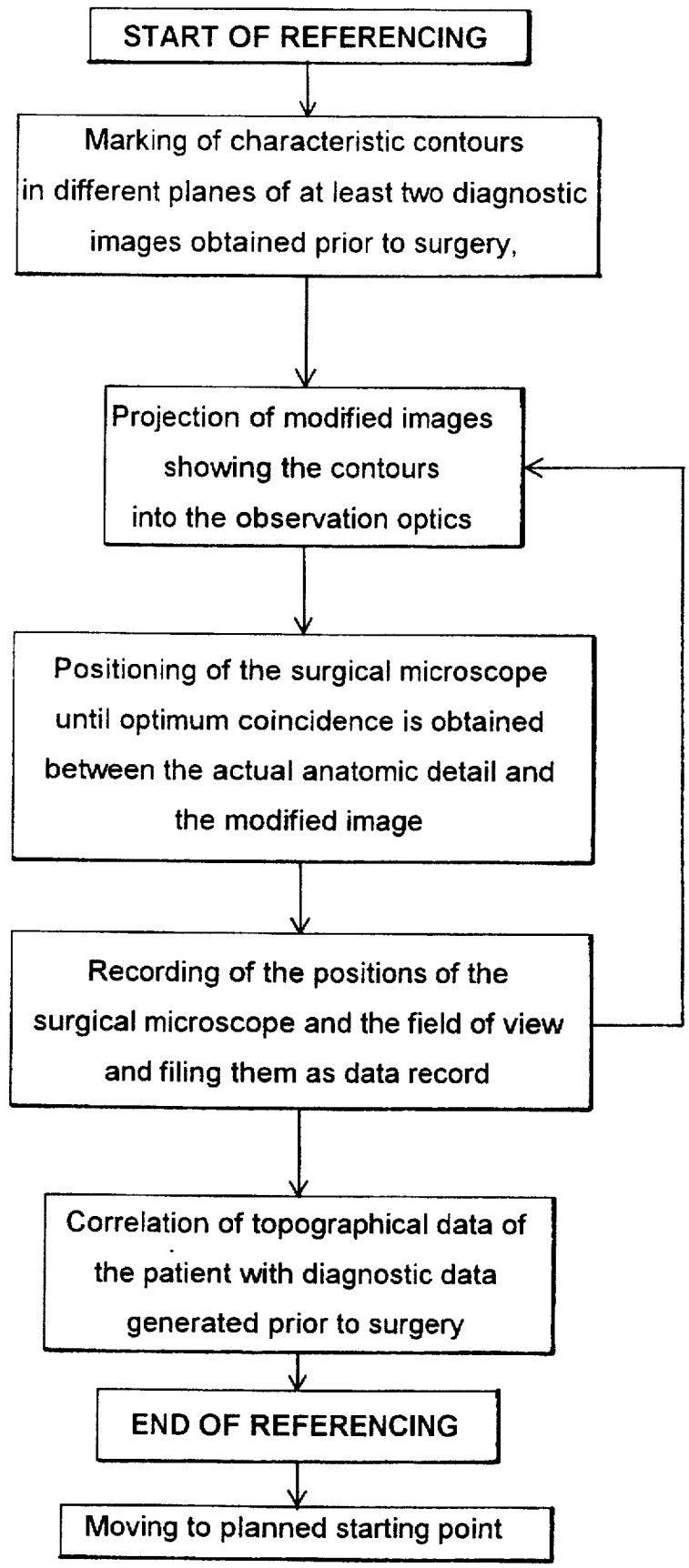
FIG. 3a shows a flow diagram of a second embodiment of the procedure according to the invention.

Another embodiment of the procedure according to the invention for the correlation of different coordinate systems using a surgical microscope without the use of additional markers is explained in FIGS. 3a and 3b.

Before the actual surgery, specific anatomical details in the body area of interest are provided with contours at the central control unit in at least two images of the diagnostic data record generated prior to surgery, which correspond to different sectional planes. If brain surgery is planned, for example, the circumference of the patient's head or the contour of one ear can be marked as contours in two images. Such modified images are then digitized and also filed in the image data base.

A modified image, which now only has these contours left on it, is then projected into the observation optics via a projection device of the surgical microscope and thus superimposed on the field of view under observation. Next, the surgical microscope mounted on the carrier system is shifted manually by the user above the patient's object area of interest until the contour of the projected, modified image coincides with the appropriate anatomic detail of the patient in the field of view, or until the contours coincide. When optimum coincidence has been obtained, the spatial coordinates of the surgical microscope and the appertaining field of view orientation and position are picked up by the central control unit and filed as an initial data record. The determination of the coordinates of the surgical microscope position including the field of view is performed in the known way via the central control unit, which evaluates the coordinate information of the carrier system and the information of the position detection system.

Manual positioning of the surgical microscope is effected via a control element operated by the user, this element permitting the surgical microscope mounted on a motorized carrier system to be controlled in a defined manner. A handle, similar to a joystick, or the like can, for example, be used for this purpose.

The second filed and modified image is processed in a completely identical manner; subsequently the second recorded data record relating to the determined position of the surgical microscope and the appertaining field of view orientation and position are also filed.

With two spatial positions of the surgical microscope, including the field of view orientation and position, being known relative to the contours, the necessary referencing or correlation of the coordinate system can then be performed. On completion of correlation by the control unit, the referencing procedure is finished and the planned starting position for surgery is assumed as in the previously described embodiment of the procedure according to the invention.

As an alternative to manual spatial positioning of the surgical microscope using the control element, this embodiment of the procedure according to the invention makes it possible to move the surgical microscope mounted on the motorized carrier system automatically over the object area of interest. During this process, the object area covered is recorded and real-time matching procedures are performed with the modified contour images. When optimum coincidence of the contours in the modified images and the anatomic details in the field of view has been obtained, the position of the surgical microscope and the field of view is recorded, etc., as in the previously described procedure. For this embodiment of the procedure according to the invention, the field of view must be continuously recorded during the scanning motion by means of a video camera, for example. The video camera or other suitable electron-optical image detectors can be advantageously arranged in a documentation beam path of the surgical microscope, for example.

FIG. 3b shows a presentation of the display (5) of the central control unit in which the contour of a specific characteristic anatomic detail (6)—in this case an ear of the patient—has been marked in a diagnostic image produced prior to surgery. This modified image is digitized and filed together with the coordinate data.

In the procedure according to the invention, this image is then projected into the observation optics of the surgical microscope, and at the same time the surgical microscope is displaced manually or automatically via the carrier system until this contour coincides as far as possible with the actual anatomic detail.

As an alternative to the embodiment of the procedure according to the invention described last, another embodiment for the collection of partial topographical information makes it possible with the help of the surgical microscope to work without the marking of anatomic details of interest and to measure points in the object area under observation directly using the surgical microscope if these points can clearly be recognized and identified both in the field of view and in the corresponding diagnostic image.

Figure 4:
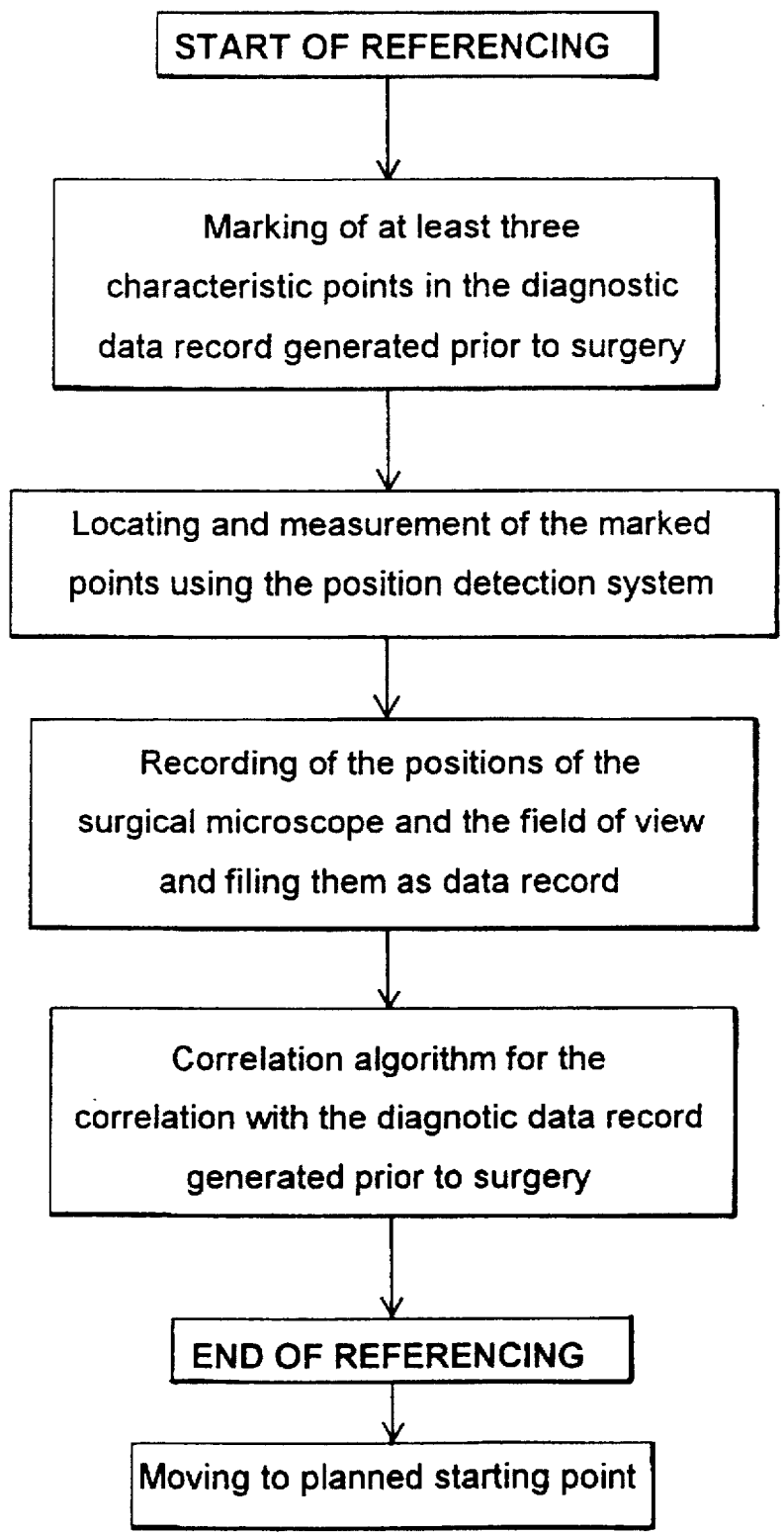
FIG. 4 shows a flow diagram of a third embodiment of the procedure according to the invention.

A flow diagram displaying the basic procedural steps of this is shown in FIG. 4. In this case, at least three characteristic points in a image of the are first marked by means of the control unit before surgery. It is necessary, of course, to choose a image of the diagnostic data record which concerns at least part of the object area also observed subsequently through the surgical microscope. Then, the surgical microscope mounted on the carrier system is positioned in space so that the clearly identifiable points are located in the field of view. By means of the position detection system of these points are then measured in their coordinates with the position of the surgical microscope being recorded simultaneously.

The subsequent correlation with the diagnostic data record generated prior to surgery is then performed in the known manner.

The identification of the characteristic points can be performed like in the previously described embodiment by manual manoeuvring of the surgical microscope over the relevant object area and by appropriate assigning of these points through the user. As an alternative, an automated procedure including the automatic recognition of these points is possible again if the surgical microscope is equipped with a suitable electro-optical image detector and a motorized carrier system is provided.

The collection of partial topographical information by the embodiment of the procedure according to the invention described last can be beneficially used intraoperatively if during brain surgery, for example, brain shifts occur, necessitating re-referencing of the field of view under observation to the diagnostic data records generated prior to surgery.

We claim:

1. A method for correlation of different coordinate systems in computer-supported stereotactic surgery without use of referencing markers, comprising:
   moving a surgical microscope (1) mounted on a carrier system (2) over a specific surface area of an object under observation,
   continually measuring distances between surface points on said surface area and said surgical microscope point-by-point to generate a three-dimensional surface profile of said surface area, and
   spatially correlating said three-dimensional surface profile with diagnostic data generated prior to surgery via a correlation algorithm.

2. The method according to claim 1, further comprising maneuvering said surgical microscope manually over said surface area of an object.

3. The method according to claim 1, further comprising automatically positioning said surgical microscope (1) mounted on a motorized carrier, over said surface area of an object by means of a central control unit (3) according to defined, preselected positioning parameters.

4. A method for correlation of different coordinate systems in computer supported stereotactic surgery without use of referencing markers, comprising:

using a surgical microscope (1) mounted on a carrier system (2), providing specific anatomic details of a field of view under observation with at least one contour (6) in diagnostic data generated prior to surgery, projecting said at least one contour (6) into observation optics of said surgical microscope (1), and positioning said surgical microscope (1) over said field of view under observation by means of said carrier system (2) so as to obtain optimum coincidence between said at least one contour (6) and a viewed object structure.

5. The method according to claim 4, further comprising manually maneuvering said surgical microscope, and performing continuous visual checks for optimum coincidence between said projected at least one contour (6) and said viewed object structure.

6. The method according to claim 4, further comprising:

maneuvering said surgical microscope (1) mounted on a carrier system by means of a central control unit (3), and continuously automatically checking maintenance of optimum coincidence between said at least one contour projected into observation optics of said surgical microscope and said viewed object structure, wherein a respective field of view is continuously measured by electro-optical detectors and processed in digitized form.

* * * * *